(12) United States Patent
Kraft

(10) Patent No.: US 7,357,046 B2
(45) Date of Patent: Apr. 15, 2008

(54) METHOD FOR DISSOLUTION TESTING OF A PHARMACEUTICAL DELIVERY DEVICE

(75) Inventor: Rainer Kraft, Castrop-Rauxel (DE)

(73) Assignee: N. V. Organon, Oss (NL)

( * ) Notice: Subject to any disclaimer, the term of this patent is extended or adjusted under 35 U.S.C. 154(b) by 180 days.

(21) Appl. No.: 10/538,988

(22) PCT Filed: Dec. 9, 2003

(86) PCT No.: PCT/EP03/50969

§ 371 (c)(1),
(2), (4) Date: Jul. 13, 2005

(87) PCT Pub. No.: WO2004/055209

PCT Pub. Date: Jul. 1, 2004

(65) Prior Publication Data

US 2006/0005641 A1   Jan. 12, 2006

Related U.S. Application Data

(60) Provisional application No. 60/433,676, filed on Dec. 16, 2002.

(30) Foreign Application Priority Data

Dec. 16, 2002   (EP) .................. 02102772

(51) Int. Cl.
*G01N 33/15* (2006.01)
(52) U.S. Cl. ........................................ 73/866
(58) Field of Classification Search ............ 73/866
See application file for complete search history.

(56) References Cited

U.S. PATENT DOCUMENTS

| | | | |
|---|---|---|---|
| 3,572,648 A | 3/1971 | Hanson | 259/90 |
| 3,801,280 A | 4/1974 | Shah et al. | 23/230 R |
| 4,237,885 A | 12/1980 | Wong et al. | 128/260 |
| 4,292,965 A | 10/1981 | Nash et al. | 128/260 |
| 4,596,576 A | 6/1986 | de Nijs | 604/892 |

(Continued)

FOREIGN PATENT DOCUMENTS

DE   197 25 105 A1   5/1998

(Continued)

OTHER PUBLICATIONS

International Search Report Application No. PCT/EP 03/50969 dated Apr. 29, 2004.

(Continued)

*Primary Examiner*—Hezron Williams
*Assistant Examiner*—Nashmiya Fayyaz
(74) *Attorney, Agent, or Firm*—Susan Hess

(57) ABSTRACT

The invention relates to a vessel for dissolution testing of a pharmaceutical delivery device, comprising: an inert vessel wall and an inert vessel bottom such that the vessel is able to hold a fluid medium; an inert retainer provided by or at the vessel wall or vessel bottom, for holding a pharmaceutical delivery device; and which retainer allows a passageway to the vessel bottom for a sampling tube. The invention further relates to a method for preparing such a vessel; a dissolution method using such a vessel and an apparatus comprising such a vessel.

1 Claim, 8 Drawing Sheets

U.S. PATENT DOCUMENTS

| | | |
|---|---|---|
| 5,412,979 A | 5/1995 | Fassihi .................. 73/53.01 |
| 5,796,016 A | 8/1998 | Müller ..................... 73/866 |
| 5,827,984 A | 10/1998 | Sinnreich et al. ............. 73/866 |
| 5,989,581 A | 11/1999 | Groenewegen ............. 424/433 |

FOREIGN PATENT DOCUMENTS

| | | |
|---|---|---|
| DE | 198 39 398 A1 | 3/2000 |
| DE | 198 80 832 C1 | 6/2001 |
| EP | 0 050 867 B1 | 5/1982 |
| EP | 0 876 815 B1 | 11/1998 |
| WO | WO 96/28717 | 9/1996 |
| WO | WO 97/02015 | 1/1997 |
| WO | WO 98/57144 | 12/1998 |
| WO | WO 00/13012 | 3/2000 |

OTHER PUBLICATIONS

Derwent Abstract No. 011825869 abstracting DE 197 25 105 A1.

METHOD FOR DISSOLUTION TESTING OF A PHARMACEUTICAL DELIVERY DEVICE

This application claims priority based on International Patent Application No. PCT/EP2003/050969, filed Dec. 9, 2003, European Patent Application No. 02102772.7, filed Dec. 16, 2002, and U.S. patent application Ser. No. 60/433,676, filed Dec. 16, 2002.

This invention relates to a vessel, method and apparatus for dissolution testing of a pharmaceutical delivery device, and more particular such a vessel, method and apparatus for testing the dissolution of an annular pharmaceutical delivery device, which floats in a fluid medium.

Dissolution testing as such is well known in the art and is for example described in "Remington: The Science and Practice of Pharmacy", 20$^{th}$ edition, edited by Alfonso R. Gennaro et al., published by Lippincott, Williams & Wilkens, in 2000. Dissolution testing is commonly carried out during pharmaceutical formulation development, stability determination, analytical development, quality control, to establish batch-to-batch consistency or as a means by which to correlate in-vitro and in-vivo drug release characteristics.

U.S. Pat. No. 5,412,979 relates to a vessel, method and apparatus for dissolution testing of a swellable dosage form, which floats in a fluid medium. The vessel comprises a disk, adapted to engage the vessel wall at a location approximately 40 millimeters from the lowermost portion of the bottom of the vessel. The disk has an annular ring assembly, which circumferentially encloses a screen mesh. The swellable dosage form is retained in the space below the screen mesh and the vessel bottom.

WO-A-9628717 also relates to a dissolution testing vessel comprising an inserted mesh or grille to prevent a formulation undergoing dissolution testing from floating freely at the surface of the testing medium. In one embodiment the inserted mesh or grille rests on one or more projections which project inwardly from the interior wall of the vessel.

The presence of the mesh screen is disadvantageous when samples are to be taken. Furthermore, dissolution testing of pharmaceutical delivery devices can require sink conditions, in which case the mesh screen is also disadvantageous. To obtain such sink conditions the dissolution vessel is to be regularly emptied and refilled with fresh dissolution medium during the testing period. When samples are taken manually and/or the dissolution vessel is emptied manually, the mesh screen can be removed manually before sampling and/or emptying. Such an act is, however, troublesome. Furthermore care should be taken to place the mesh screen back in the correct position. When samples are taken automatically and/or the dissolution vessel is emptied automatically, samples cannot be taken in the lower part of the dissolution vessel and the lower part of the dissolution vessel cannot be emptied. An additional disadvantage is that the screen mesh is held loosely in the vessel, and can change position during dissolution testing. The vessel comprising the mesh screen is further disadvantageous for dissolution testing of relatively large dosage forms, which can be pressed against the mesh screen and be damaged.

Therefore, an improved vessel, method and apparatus for dissolution testing of a pharmaceutical delivery device is desirable.

The present invention provides a vessel for dissolution testing of a pharmaceutical delivery device, comprising:

an inert vessel wall and an inert vessel bottom such that the vessel is able to hold a fluid medium;

an inert retainer provided by or at the vessel wall or vessel bottom, for holding a pharmaceutical delivery device; and which retainer allows a passageway to the vessel bottom for a sampling tube.

The present invention further provides a method for preparing such a vessel comprising melting or gluing the retainer to the vessel wall or vessel bottom or by applying one or more indentations to the vessel wall or vessel bottom.

The present invention further provides a method for dissolution testing of a pharmaceutical delivery device, which delivery device contains a pharmaceutically and/or contraceptive effective amount of drug, comprising:

placing a fluid medium and stirring means in a dissolution vessel according to the invention;

placing a pharmaceutical delivery device in the retainer of the dissolution vessel according to the invention;

rotating the stirring means to circulate the fluid medium in the dissolution vessel;

sampling one or more predetermined volumes of the fluid medium at selected time intervals by means of a sampling tube.

The present invention further provides an apparatus for dissolution testing of a pharmaceutical delivery device, comprising:

one or more dissolution vessels according to the invention which dissolution vessels are suitable for holding a fluid medium;

one or more stirring means;

a sampling and/or discharging device with one or more sampling and/or discharging tubes suitable for sampling and/or discharging one or more predetermined volume fractions of the fluid medium from the dissolution vessels; and optionally, a refilling device suitable for adding fluid medium to the dissolution vessels.

The following drawings have been enclosed to illustrate the present invention. Elements, which are substantially identical, and elements, which perform substantially the same function, are denoted in the figures by the same numerals.

Figure 3A:
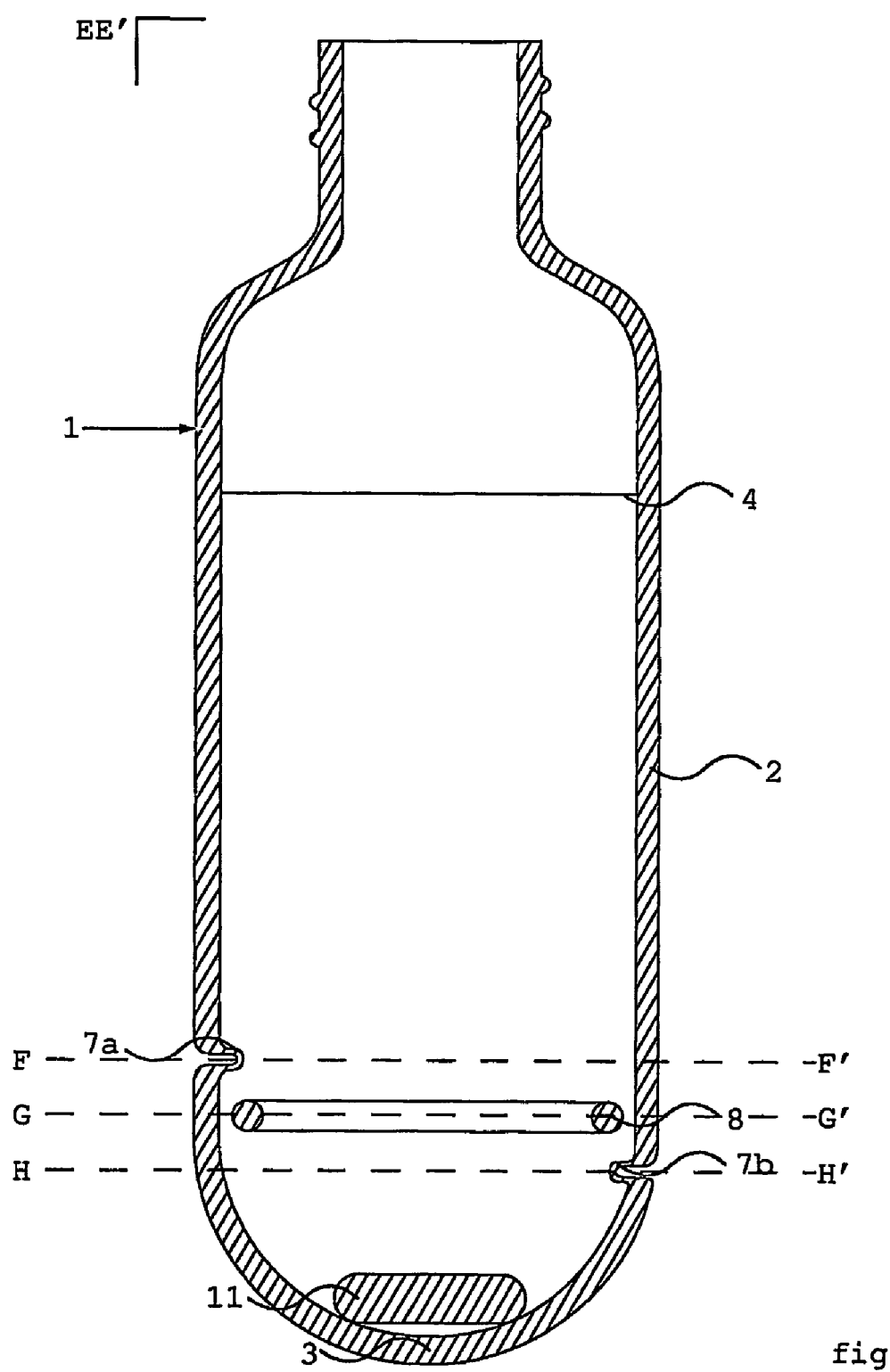
FIG. 3A is a cross-sectional side-view of a third embodiment of a dissolution vessel according to the invention.
Figure 3B:
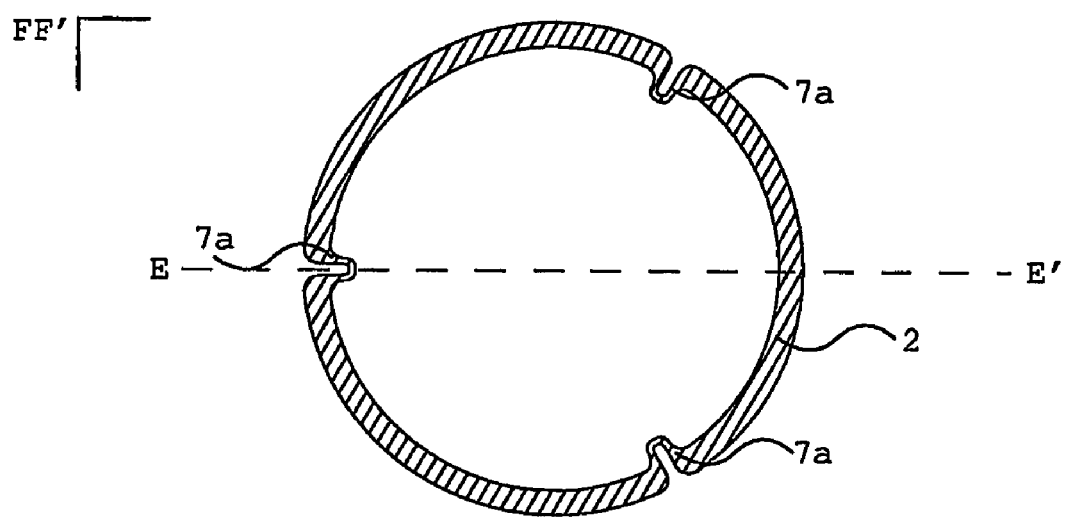
Figure 3C:
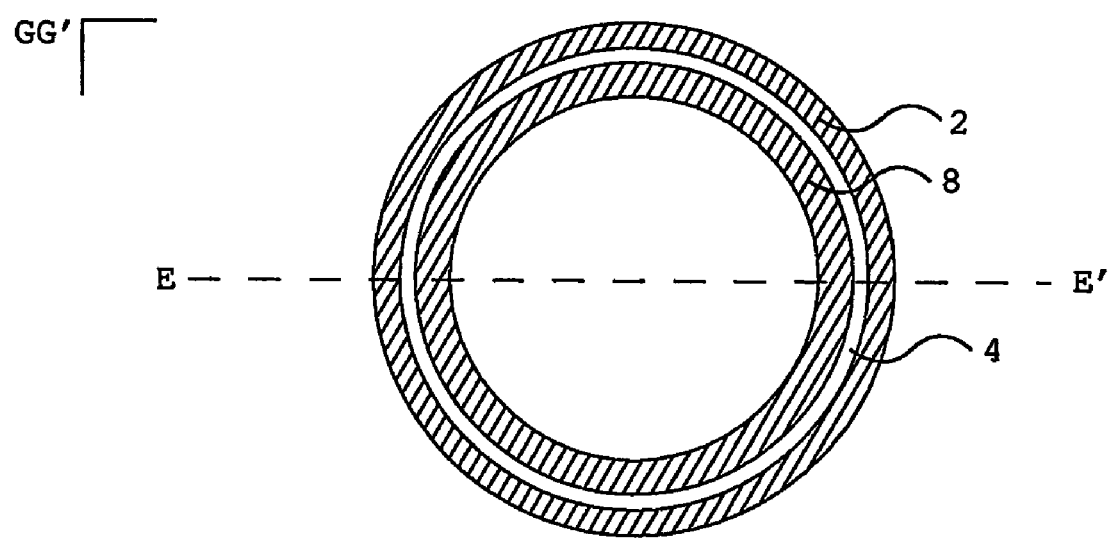
Figure 3D:
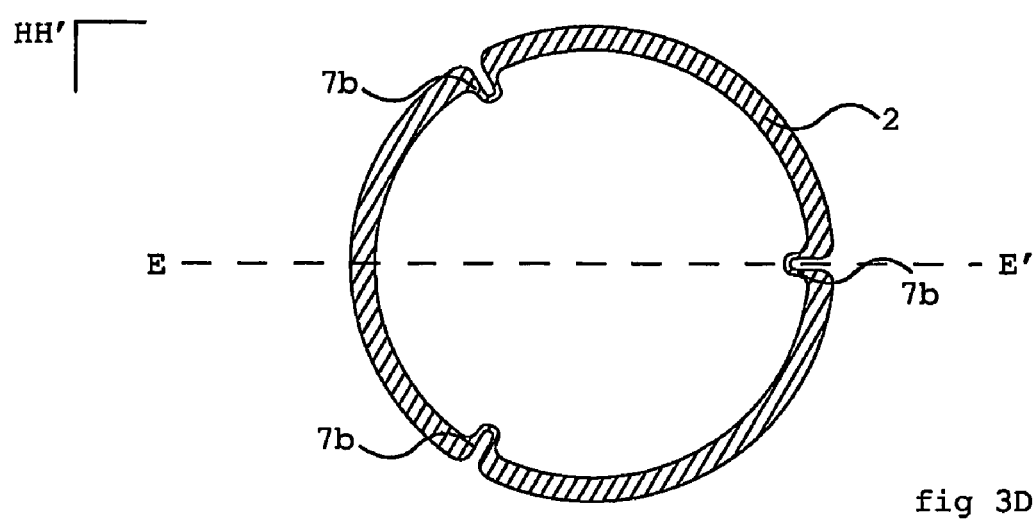

FIG. 3B to 3D respectively show cross-sectional top-views of the vessel according to FIG. 3A.

Figure 1A:
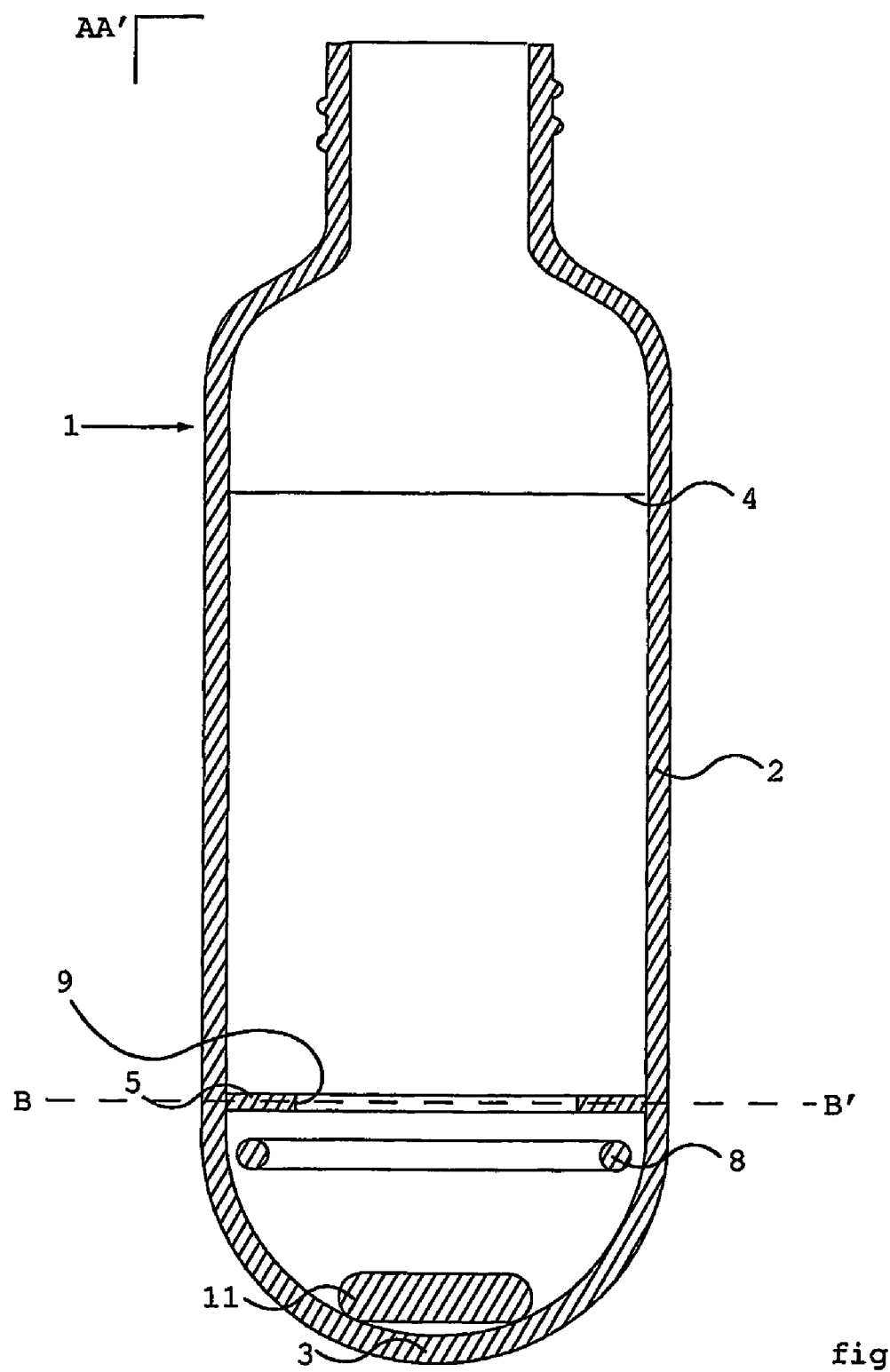
FIG. 1A is a cross-sectional side-view of a first embodiment of a dissolution vessel according to the invention.

Referring to FIG. 1A, the vessel for dissolution testing (1) comprises a vessel wall (2) and a vessel bottom (3) such that the vessel is able to hold a fluid medium (4). The vessel wall (2) and the vessel bottom (3) are made from an inert material. By an inert material is understood a material which essentially does not sorb, react or interfere in or with the pharmaceutical delivery device being tested. In a further embodiment the material from which the vessel wall (2) and/or the vessel bottom (3) are prepared is a transparent material. The vessel wall (2) and the vessel bottom (3) can be made from different types of inert material or from the same type of inert material. In an even further embodiment both the vessel wall (2) and the vessel bottom (3) are made from the same type of inert material. In an even further embodiment the vessel wall (2) and the vessel bottom (3)

form one entity, wherein the vessel wall (2) gradually changes into the vessel bottom (3). Examples of suitable materials include glass or an inert plastic. In another embodiment the material is glass. In a further embodiment the vessel wall (2) and vessel bottom (3) form one transparent glass entity.

In another embodiment the dissolution vessel (1) is cylindrically shaped with a hemispherical bottom. Here, the vessel wall (2) is understood to be the cylindrically shaped part of the vessel and the vessel bottom (3) is understood to be the hemispherical shaped part of the vessel. The height and inside diameter of the dissolution vessel (1) can be varied widely and can be adapted such that the desired volume of fluid medium (4) can be held. For example, the United States Pharmacopeia describes a height in the range from 160 to 210 mm and an inside diameter from 98 to 106 mm for a dissolution vessel holding 1 L of liquid medium. In one embodiment the height of the dissolution vessel (1) lies in the range of 5 to 30 cm, in a further embodiment it lies in the range of 10 to 25 cm, and in an even further embodiment it lies in the range of 10 to 20 cm. In another embodiment the inside diameter of the dissolution vessel lies in the range of 2 to 15 cm, in a further embodiment it lies in the range of 3 to 11 cm, and in an even further embodiment it lies in the range of 5 to 8 cm.

The vessel (1) is able to hold a fluid medium (4). The fluid medium (4) can be any medium suitable for dissolution testing, including for example, organic solvents such as alkanols and esters; water; acidic solutions, such as for example aqueous solutions of hydrochloric acid; and phosphate buffers. The fluid medium (4) can be selected based upon the nature and target site of the pharmaceutical delivery device (8). For example, a fluid medium (4) can be used which is to simulate gastric fluid or intestinal fluid. In a further embodiment the fluid medium (4) is selected from the group consisting of water; dilute aqueous solutions of hydrochloric acid, such as for example HCl solutions in the range from 0.001 to 0.5N HCl, and in yet another embodiment in the range from 0.01 to 0.1N HCl; and phosphate buffers. In an even further embodiment the fluid medium is water. The pH of the fluid medium (4) can vary widely. In one embodiment the pH lies in the range from 1 to 12, and in a further embodiment the pH lies in the range from 1 to 8. In one embodiment the pH of the fluid medium (4) simulates the pH of the targeted place of dissolution in the human body. For example, to mimic the environment of the stomach, a fluid medium (4) with a pH of about 1 can be used; and to mimic the pH of the lumen of the intestine a pH of about 6.6 can be used.

Figure 2A:
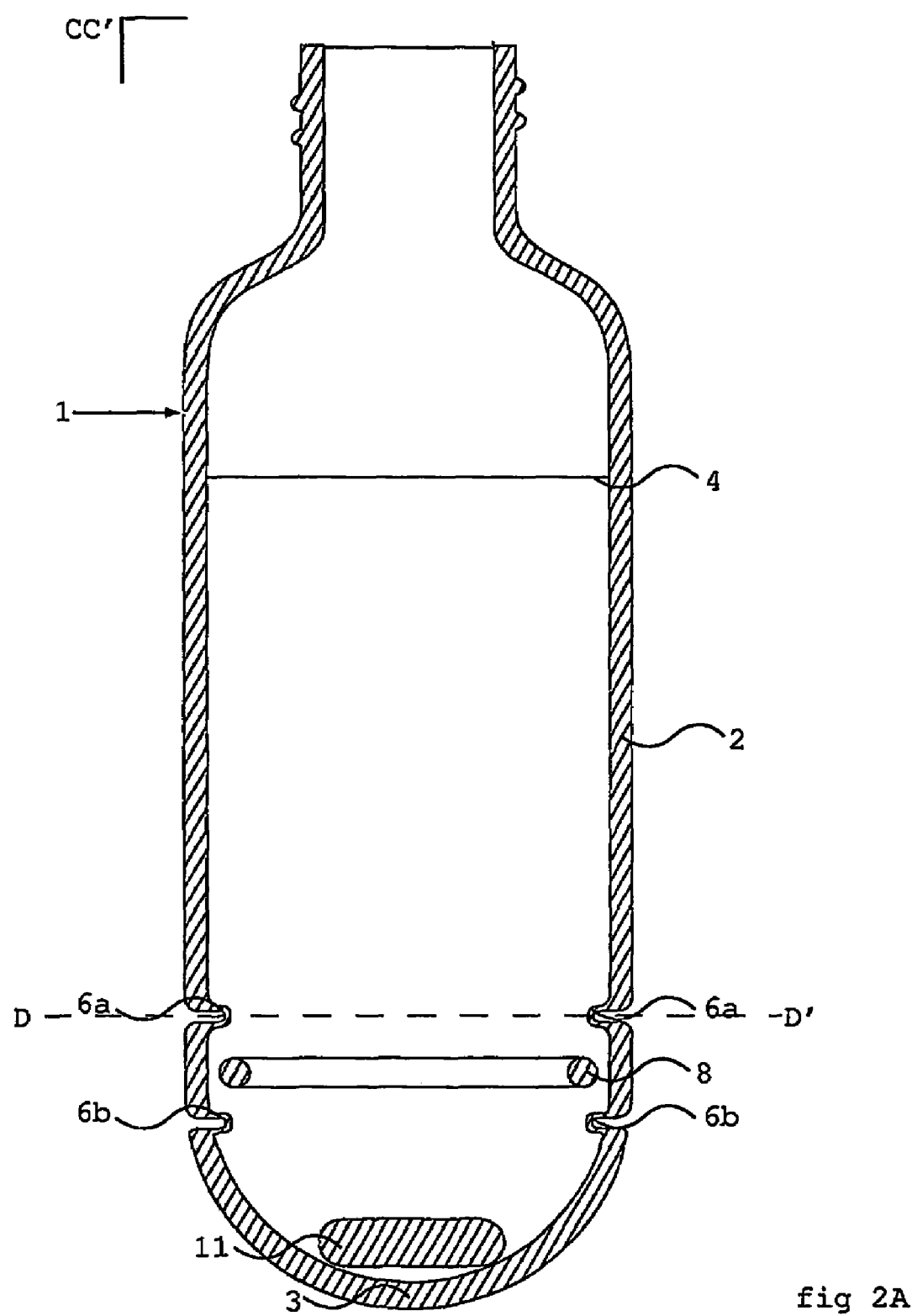
FIG. 2A is a cross-sectional side-view of a second embodiment of a dissolution vessel according to the invention.

Provided by or at the vessel wall (2) or vessel bottom (3) there is a retainer (see 5 in FIG. 1A; 6 in FIG. 2A; and 7 in FIG. 3A), which retainer (5; 6; 7) is intended for holding a pharmaceutical delivery device (See 8 in FIG. 1A) and which retainer allows a passageway to the vessel bottom (3) for a sampling tube. The dimensions of the retainer are such that a pharmaceutical delivery device can be held submerged in the dissolution medium in a suitable manner.

The retainer (5; 6; 7) is prepared from an inert material. The retainer (5; 6; 7) can be prepared from the same material as the vessel wall (2) or vessel bottom (3) or from a different material. Suitable materials include stainless steel, an inert plastic or glass. In a further embodiment the retainer is prepared from glass. In one embodiment the retainer (5; 6; 7) is located at a distance of ⅛ to ½ of the height of the dissolution vessel (1) from the vessel bottom (3). In another embodiment this distance lies in the range from 0.5 to 10 cm, and in a further embodiment this distance lies in the range of 1 to 6 cm.

Figure 1B:
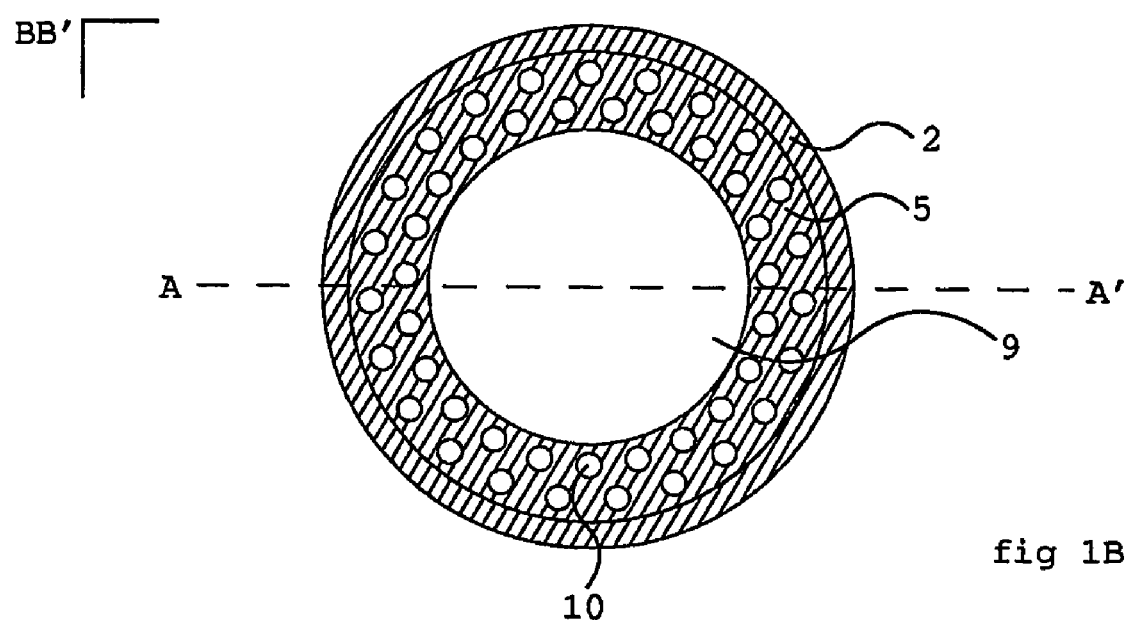
FIG. 1B is a cross-sectional top-view of the vessel according to FIG. 1A.

In one embodiment the retainer comprises an annular plate (see 5 in FIGS. 1A and 1B), which annular plate comprises a passageway (9) for a sampling tube in the middle, and which annular plate (5) is placed inside the dissolution vessel (1) at the vessel wall (2). The annular plate (5) can be made of any inert material, but in a further embodiment it is made of inert plastic, glass, stainless steel, or a combination thereof. In an even further embodiment the annular plate is manufactured from glass. The annular plate (5) can comprise a number of holes (10) to provide a better contact of the fluid medium (4) above the annular plate (5) and the fluid medium (4) below the annular plate (5).

The width of the annular plate is not critical and can be chosen such that a desired pharmaceutical delivery device (8) can be held. In one embodiment the width lies in the range of 0.2 to 6 cm, in a further embodiment the width lies in the range from 0.5 to 3 cm, and in an even further embodiment it lies in the range from 0.5 to 2 cm. The passageway (9) in the middle of the annular plate (5) has a diameter, which diameter allows a smooth passage for a sampling tube. In a further embodiment the diameter of the passageway (9) is therefore at least 1 cm, and in an even further embodiment at least 2 cm; in yet an even further embodiment it is at least 3 cm. In another embodiment, diameters up to 20 cm are used; in another embodiment diameters up to 10 cm are used, and in yet another embodiment diameters up to 6 cm are used. Use of the separate annular plate (5) as described, however, has the disadvantage that the retainer is fitted loosely in the dissolution vessel (1), and can change position during dissolution testing.

Figure 2B:
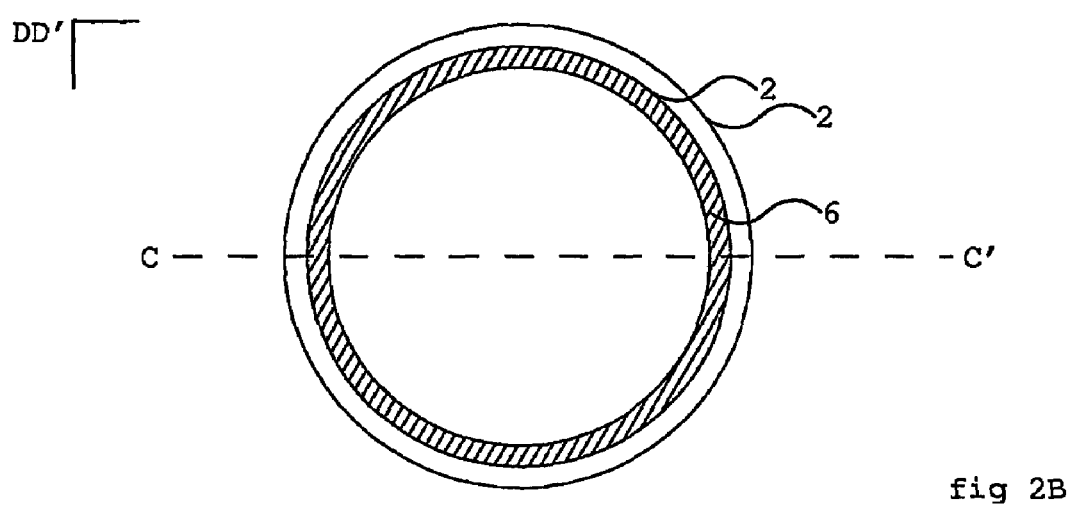
FIG. 2B is a cross-sectional top-view of the vessel according to FIG. 2A.

In a further embodiment therefore, the retainer is provided by the vessel wall (2) or vessel bottom (3) itself, that is, it is permanently fixed to the vessel wall (2) or vessel bottom (3). In a further embodiment such a retainer is provided by the vessel wall (2), where the vessel wall is understood to be that part of the vessel which forms the (essentially vertical) sides of the vessel. Such a retainer (see 6 in FIGS. 2A; and 7 in FIG. 3A) can have any form suitable for holding a pharmaceutical delivery device (8) and allowing a passageway (9) to the vessel bottom (3) for a sampling tube. Suitable ranges for the diameter of the passageway (9) include those that are described above. In one embodiment the retainer comprises one or more annular ledges or rims (see 6 in FIGS. 2A and 2B); one or more bulges (see 7 in FIG. 3A, FIG. 3B and FIG. 3C); one or more hooks (not shown) or a combination thereof. The annular ledges or rims (6), bulges (7) or hooks are protruding inwardly from the vessel wall (2) or vessel bottom (3). The bulges (7) and hooks have the further advantage that the contact between the retainer and the tested pharmaceutical delivery device is kept to a minimum.

In a further embodiment the retainer consists of two elements provided by the vessel wall (2) or vessel bottom (3), one upper element and one lower element. In an even further embodiment both these elements are protruding inwardly from the vessel wall (2) or vessel bottom (3). In one embodiment the retainer comprises two annular ledges or rims (see 6a and 6b in FIG. 2A) or two sets of bulges (see 7a and 7b in FIG. 3A); one upper annular ledge or rim (6a) or upper set of bulges (7a), and one lower annular ledge or rim (6b) or lower set of bulges (7b).

In a further embodiment each set of bulges or hooks comprises from 2 to 50 bulges or hooks, in a yet further embodiment each set comprises from 2 to 10 bulges or hooks and in a still further embodiment from 3 to 5 bulges or hooks. In another embodiment the bulges (7) within one set are located equidistantially from each other.

Furthermore in yet another embodiment, an upper set of bulges (see 7*a* in FIG. 3A and FIG. 3B), is located in a staggered position with regard to a lower set of bulges (see 7*b* in FIG. 3A and FIG. 3D). In a further embodiment the distance between an upper annular ledge or rim (6*a*) and a lower annular ledge or rim (6*b*); or between an upper set of bulges (7*a*) and a lower set of bulges (7*b*), is such that a pharmaceutical delivery device (8) can be loosely held in between. In one embodiment, this distance lies in the range from 0.5 to 4 cm, and in a further embodiment this distance lies in the range from 1 to 3 cm.

As described above the pharmaceutical delivery device (8) can be located between two annular ledges or rims (see 6 in FIG. 2A); between two sets of bulges (see 7 in FIG. 3A); or within one set of hooks. The width of the annular ledge or rim can be chosen such that a desired pharmaceutical delivery device (8) can be held. In one embodiment the width of such an annular ledge or rim (6) lies in the range of 0.05 to 3 cm, in a further embodiment the width lies in the range of 0.1 to 2 cm, and in an even further embodiment in the range from 0.2 to 1.5 cm. Similarly the height of the bulges (7) or hooks in the direction protruding inwardly perpendicular to the vessel wall (2) or vessel bottom (3) can be chosen such that a desired pharmaceutical delivery device (8) can be held. In one embodiment the height lies in the range of 0.05 to 3 cm, in a further embodiment the height lies in the range of 0.1 to 1.5 cm, and in an even further embodiment in the range from 0.2 to 1.0 cm.

The retainer (6; 7) can be permanently fixed to the vessel wall (2) or vessel bottom (3) by, for example, gluing or melting, after the dissolution vessel (1) itself has already been manufactured. Alternatively, the retainer (6; 7) can be permanently fixed to the vessel wall (2) or vessel bottom (3) during manufacture of the dissolution vessel itself. In this embodiment the material of the retainer can be the same or a different material from the material of the vessel wall (2) or vessel bottom (3). In another embodiment the retainer and vessel wall (2) or vessel bottom (3) are manufactured from the same material, which material is in yet another embodiment glass or an inert plastic and in even a further embodiment the material is glass.

In a further embodiment, the retainer is part of the vessel wall (2) or vessel bottom (3) and is provided by one or more indentations of the vessel wall or vessel bottom. Such an indentation can be circular, resulting in an annular ledge or rim (6); or pointed, resulting in a bulge (7). The indentation or indentations can be applied during the manufacture of the dissolution vessel (1) or afterwards.

This invention therefore also provides a method for preparing the dissolution vessel according to the invention by melting or gluing a retainer to a vessel wall or vessel bottom as described above or by applying one or more indentations in a vessel wall or vessel bottom as described above.

In a further embodiment, the indentation is applied by warming the material of the vessel wall (2) or vessel bottom (3) to an elevated temperature where the material becomes soft; and subsequently pressing the material inwardly to a sufficient extent. In yet a further embodiment, the retainer comprises two sets of 3 bulges (see 7*a* and 7*b* in FIG. 3A), viz. one upper set and one lower set in a staggered position, formed by indentation of the vessel wall (2) or vessel bottom (3).

The vessel according to the invention is suitable for testing the dissolution of a wide range of pharmaceutical delivery devices (8). The vessel according to the invention is, however, especially suitable for testing the dissolution of a pharmaceutical delivery device (8) having an annular shape (i.e. a ring-shaped device). The outside diameter and the thickness of the annular pharmaceutical delivery device can vary widely. In one embodiment, the outside diameter lies in the range from 3 to 10 cm, and in a further embodiment the outside diameter lies in the range of 4 to 8 cm; and in another embodiment the thickness lies in the range from 0.1 cm to 1 cm and in a further embodiment the thickness lies in the range from 0.2 cm to 0.7 cm. In a further embodiment the annular pharmaceutical delivery device (8) is made of a flexible material, such that it can easily be placed inside the retainer (5; 6; 7). In one embodiment, when testing the dissolution of such an annular pharmaceutical device, a vessel according to the invention is used having an inner diameter slightly larger than the outer diameter of the annular pharmaceutical device, wherein the ratio from the inner diameter of the dissolution vessel according to the invention to the outer diameter of the annular pharmaceutical delivery device lies in the range from 1.0001:1 to 1.5:1, and in a further embodiment lies in the range from 1.005:1 to 1.1:1.

The dissolution vessel according to the invention is further especially suitable for dissolution testing of annular pharmaceutical delivery devices, which float in the fluid medium. Such a tendency to float could, for example, be due to the inactive ingredients used. In one embodiment the annular pharmaceutical delivery device is a flexible annular pharmaceutical delivery device comprising at least one compartment which comprises a thermoplastic polymer core and a thermoplastic polymer skin covering the core, which core comprises a mixture of a progestogenic compound and an estrogenic compound, and which skin is permeable for the progestogenic and estrogenic compounds.

Examples of annular pharmaceutical delivery devices for which the dissolution vessel according to the invention is especially suitable include the annular pharmaceutical delivery devices described in for example U.S. Pat. No. 5,989,581, WO-A-97/02015, U.S. Pat. No. 4,237,885, EP-A-0876815, EP-A-0050867, U.S. Pat. No. 4,292,965, U.S. Pat. No. 4,596,576, which are hereby incorporated by reference.

In addition to the above, one or more stirring means (11) can be present. Such stirring means (11) can be any means known in the art for stirring the fluid medium in the dissolution vessel and include for example paddles and magnetic stirrers. In one specific embodiment a magnetic stirrer is used.

This invention further provides a method for dissolution testing of pharmaceutical delivery device, which delivery device contains a pharmaceutical and/or contraceptive effective amount of drug, comprising:

placing a fluid medium and stirring means in a dissolution vessel according to this invention;

placing a pharmaceutical delivery device in the retainer of the dissolution vessel according to this invention;

rotating the stirring means to circulate the fluid medium in the dissolution vessel;

sampling one or more predetermined volumes of the fluid medium at selected time intervals by means of a sampling tube.

The pharmaceutical delivery device can be any delivery device known in the art, but in a specific embodiment it is an annular delivery device as described above. In a further embodiment the pharmaceutical delivery device is an annular delivery device as described in U.S. Pat. No. 5,989,581.

The fluid medium can be any fluid medium suitable for dissolution testing. In a further embodiment, however, it is a fluid medium as described above. In a further embodiment water is used as a fluid medium. The amount of fluid medium used can be chosen such to enable the dissolution measurement of the specific drug concentration in the pharmaceutical delivery device. In one embodiment the volume lies in the range of 25 to 1000 ml, in a further embodiment the volume lies in the range from 50 to 500 ml. In yet a further embodiment, volumes of 100 ml or 200 ml are used. The temperature of the fluid medium can vary widely, but in a further embodiment the temperature is similar to the temperature of the human body and lies in the range from 36° C. to 38° C., and in an even further embodiment the temperature lies in the range from 36.5° C. to 37.5° C. The temperature of the fluid medium can be maintained by any manner known in the art, including, for example by means of a water bath or by means of heating jacket.

Suitable stirring means are as described above.

The fluid medium is sampled by means of a sampling tube. The sampling times can be chosen such that a sufficient amount of samples is taken during the release time of drug from the pharmaceutical delivery device. The exact time intervals will depend on the release time of the drug from the pharmaceutical delivery device. For example, if an immediate release delivery device is tested, time intervals can, for example, lie in a range from 1 minute to 1 hour. If a slow-release delivery device is tested, such time intervals can, for example, lie in the range from 0.5 hour to 48 hours. Depending on the goal of the dissolution test the sampling can take place only once or more often. In one embodiment the fluid medium is sampled only once, and it is sampled after in the range from 50 to 100% of the drug has been released. In a further embodiment the fluid medium is sampled in the range from 1 to 30 times during the release time of drug from the pharmaceutical delivery device, in an even further embodiment the fluid medium is sampled in the range from 3 to 20 times and in an even further embodiment the fluid medium is sampled in the range from 4 to 15 times.

If it is necessary to obtain sink conditions, in a further embodiment the steps of discharging the total of fluid medium from the dissolution vessel and refilling the dissolution vessel with fresh fluid medium after sampling, are added. The fluid medium can be discharged from the dissolution vessel by means of a discharging tube. Similarly, the dissolution vessel can be refilled with fresh fluid medium via a refilling tube. In another embodiment the sampling tube as described above is used as discharging tube and/or refilling tube, when necessary.

The samples taken are to be analysed to establish the drug concentration at the sampling moment. The samples can be analysed after all samples have been taken, but in another embodiment they are analysed directly after sampling. The samples can be analysed by using any method known in the art to be suitable therefore. Examples of possible analyse techniques include fluorescence, indirect or direct ultraviolet (UV), Infrared (IR), refractometry, scattering techniques, near-Infrared (NIR), electrochemical and/or Raman spectroscopy techniques.

Furthermore this invention provides an apparatus for dissolution testing of a pharmaceutical delivery device, comprising:

one or more dissolution vessels according to the invention, which dissolution vessels are suitable for holding a fluid medium;

one or more stirring means;

a sampling and/or discharging device with one or more sampling and/or discharging tubes suitable for sampling and/or discharging one or more predetermined volume fractions of the fluid medium from the dissolution vessels; and optionally, a refilling device suitable for adding fluid medium to the dissolution vessels.

The sampling and/or discharging device can be used to take one predetermined volume fraction of the fluid medium for sampling purposes or to take a series of predetermined volume fractions to discharge the total of fluid medium from the dissolution vessel. In a further embodiment the discharging device and the refilling device are one and the same device, which device can be operated in two opposite directions, viz. to transfer fluid medium from the dissolution vessels to a predetermined discharging position and to transfer fluid medium from a predetermined storing position to the dissolution vessels.

The apparatus according to the invention can be used in a set-up comprising in addition an analytical device. The analytical device can be a device for measuring the drug concentration in a sample of the fluid medium by fluorescence, ultraviolet (UV), Infrared (IR), near-Infrared (NIR), electrochemical and/or Raman spectroscopy techniques.

The apparatus can be operated manually or automatically. In another embodiment of the invention, however, the apparatus is operated automatically, wherein a motor, directed by a computing device, operates the stirring means, the sampling and/or discharging device and/or refilling device. In a further embodiment any samples are further transferred automatically to an analytical device, where they are automatically analysed. In an even further embodiment the analytical data is subsequently gathered automatically by the computing device and in yet an even further embodiment the data is automatically visualised by this same computing device.

The examples provided above are not meant to be exclusive. Many other variations of the present invention that will be readily apparent to those skilled in the art are contemplated to be encompassed within the appended claims.

The invention claimed is:

1. A method for dissolution testing of a pharmaceutical delivery device containing an amount of a drug, the method comprising:

placing a fluid medium and stirring means in a dissolution vessel comprising:
  an inert vessel wall and an inert vessel bottom such that the vessel is able to hold the fluid medium, and
  an inert retainer provided by or at the vessel wall or vessel bottom, for holding the pharmaceutical delivery device and providing a passageway to the vessel bottom for a sampling tube;

placing the pharmaceutical delivery device in the retainer;

rotating the stirring means to circulate the fluid medium in the dissolution vessel;

inserting a sampling tube through the passageway; and sampling one or more predetermined volumes of the fluid medium at selected time intervals by means of the sampling tube.

* * * * *